(12) United States Patent
Kayyali et al.

(10) Patent No.: US 12,144,581 B1
(45) Date of Patent: *Nov. 19, 2024

(54) SLEEP DIAGNOSTICS USING CELLULAR AND/OR INTERNET DATA TRANSFER FROM REMOTE TESTING LOCATIONS

(71) Applicant: Cleveland Medical Devices Inc., Cleveland, OH (US)

(72) Inventors: Hani Kayyali, Shaker Heights, OH (US); Craig A Frederick, Solon, OH (US); Daniel Bishop, Tallmadge, OH (US); Robert N Schmidt, Ft. Myers, OH (US); Brian M Kolkowski, Leroy, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/541,514

(22) Filed: Dec. 15, 2023

Related U.S. Application Data

(63) Continuation of application No. 18/198,327, filed on May 17, 2023, now Pat. No. 11,877,823, which is a continuation of application No. 18/094,433, filed on Jan. 9, 2023, now Pat. No. 11,690,512, which is a continuation of application No. 17/878,152, filed on Aug. 1, 2022, now Pat. No. 11,576,577, which is a continuation of application No. 15/867,763, filed on Jan. 11, 2018, now Pat. No. 11,432,724, which is a continuation of application No. 13/853,436, filed on Mar. 29, 2013, now abandoned, which is a continuation of application No. 11/454,482, filed on Jun. 16, 2006, now Pat. No. 8,437,843.

(51) Int. Cl.
A61B 5/00 (2006.01)
A61B 5/087 (2006.01)
A61B 5/1455 (2006.01)
A61B 5/369 (2021.01)

(52) U.S. Cl.
CPC ............ *A61B 5/0024* (2013.01); *A61B 5/087* (2013.01); *A61B 5/14551* (2013.01); *A61B 5/369* (2021.01); *A61B 5/4806* (2013.01); *A61B 5/6823* (2013.01); *A61B 5/721* (2013.01)

(58) Field of Classification Search
CPC ... A61B 5/0024; A61B 5/14551; A61B 5/369; A61B 5/4806; A61B 5/6823; A61B 5/721
USPC ......................................................... 600/324
See application file for complete search history.

(56) References Cited

U.S. PATENT DOCUMENTS 11,576,577 B1 * 2/2023 Kayyali ................. A61B 5/721

\* cited by examiner

*Primary Examiner* — Joseph M Dietrich
*Assistant Examiner* — Michael T. Holtzclaw
(74) *Attorney, Agent, or Firm* — Brian Kolkowski

(57) ABSTRACT

The present invention provides for a data acquisition system for sleep diagnostics, and method of using such system. The wireless sleep diagnostic data acquisition system can be used for remote testing, and provides for an easy and seamless transfer of testing data through cellular systems from a portable, wearable patient interface box to a computer and/or monitor to allow the patients physician to review and analyze the sleep data at one or more sites remote from where the patient was tested.

10 Claims, 5 Drawing Sheets

SLEEP DIAGNOSTICS USING CELLULAR AND/OR INTERNET DATA TRANSFER FROM REMOTE TESTING LOCATIONS

CROSS-REFERENCE TO RELATED APPLICATIONS

This application is a continuation of U.S. patent application Ser. No. 18/198,327, which was filed on May 17, 2023, and which is a continuation of U.S. patent application Ser. No. 18/094,433, which was filed on Jan. 9, 2023, issued as U.S. Pat. No. 11,690,512 on Jul. 4, 2023, and which is a continuation of U.S. patent application Ser. No. 17/878,152, which was filed on Aug. 1, 2022, issued as U.S. Pat. No. 11,576,577 on Feb. 14, 2023, and which is a continuation of U.S. patent application Ser. No. 15/867,763, which was filed on Jan. 11, 2018, issued as U.S. Pat. No. 11,432,724 on Sep. 6, 2022, and which is a continuation of U.S. patent application Ser. No. 13/853,436, which was filed on Mar. 29, 2013, and which is a continuation of U.S. patent application Ser. No. 11/454,482, which was filed on Jun. 16, 2006, and issued as U.S. Pat. No. 8,437,843 on May 7, 2013. The specifications and drawings of each of the above patents and applications are hereby incorporated by reference in their entirety.

BACKGROUND OF THE INVENTION

1. Field of the Invention

The present invention, relates generally, to wireless data acquisition systems for data communications and more particularly, to programmable wireless medical acquisition systems for remote sleep monitoring which can be adapted by software programming.

2. Technical Background

Electroencephalogram (EEG) data acquisition systems have generally, been, wired or tethered systems that operate in a similar fashion. The systems, generally, receive an external input signal from EEG electrodes and sometimes other sensing devices, and usually transmit the signal to another piece of equipment, which conditions and analyzes the signal.

Recently, wireless EEG data acquisition systems have been introduced, which receive input signals from EEG electrodes and in some situations other sensing devices, and transmit those signals to another piece of equipment. In the case of a wired system the analog input can be transmitted directly over interconnecting wiring with the major concern being that the interconnecting wires be suitably shielded to prevent interference by nearby electromagnetic sources. Signal conditioning, however, becomes critically important for wireless systems, though. This is because the sensor signals can be significantly affected both through sensor pickup and later when wirelessly transmitting the signal to a base station or other device. In addition, wireless systems are affected by interference, bandwidth problems, data transfer rates, versatility of use due to data transfer issues, signal problems, battery life and the like.

Accordingly, a need exists for a programmable wireless medical EEG data acquisition system employing small size, low power consumptive and low cost components. Additionally, a need exists for such a system which can accurately and dependably transmit data at frequencies below 2.0 GHz. Further, a need exist for such a system which can correct for motion artifacts in the EEG signals and other sensor signals. A further need exists for such a system that has the ability to accept removable memory for data storage and data buffering universally to increase versatility and future upgradeability.

SUMMARY OF THE INVENTION

The present invention provides for a data acquisition system for EEG and other physiological conditions, preferably wireless, and method of using such system. The wireless EEG system can be used in a number of applications including both studies and clinical work. These include both clinical and research sleep studies, alertness studies, emergency brain monitoring, and any other tests or studies where a subject's or patient's EEG reading is required or helpful.

The EEG data acquisition system of the present invention includes a number of features, which enhance this system over other systems presently in the marketplace. These features include but are not limited to the having multiple channels for looking at a number of physiological features of the subject or patient, a built in accelerometer for looking at a subject's or patient's body motion, a removable memory for data buffering and storage, capability of operating below 2.0 GHz, which among other things allows for increased operational range, movement artifact correction including video, EOG artifact correction, pressure sensors capable of measuring or determining airflow, tidal volume, ventilation rate, and snore detection and capability of manual and automatic RF sweep. This system further preferably has a receiver or transceiver for receiving wireless signals from a wireless data acquisition interface box with the additional features of the receiver or transceiver being powered through a computers USB port, and can receive data from multiple wireless data acquisition interface boxes concurrently preferably with little or no interference.

The software for the present invention allows the EEG data acquisition system to do a number of operations that other system can not accomplish with the same type of hardware. The use of software filtering makes it possible to determine airflow, tidal volume, ventilation rate and snore detection from a single pressure transducer. The use of software also makes most of the video related features possible. Software is used to synchronize video with physiological signals for display. Software is also used to remove EEG artifacts created by ocular movement. Software is further used to correct motion artifacts that occur, by using data acquired from accelerometers and video.

The nature of EEG signals and their relatively weak physiological signal makes EEG acquisition much more difficult than other biopotential signals, such as ECG to pick up and analyze. One of the further features of the present invention is to be able to pick up and transmit extremely sensitive signals while simultaneously analyzing signals from other types of more robust physiological sensors.

In one embodiment the invention is a wireless EEG data acquisition system comprising an interface box comprising one or more electrical components for receiving electrical signals from EEG sensors, one or more electrical components for wirelessly transmitting electrical signals, at least 1 EEG channel connected to the one or more electrical components for receiving electrical signals, and at least one sensor having a signal internal to or integrated with the interface box, wherein the sensor having a signal internal to or integrated with the interface box is an accelerometer used for measuring the subject's movements. It is most advantageous to have the accelerometer integrated with the data acquisition system to allow for motion artifact correction before transmission to the base station thereby lessening the amount of data that needs to be transmitted wirelessly.

In another embodiment the invention is a wireless EEG data acquisition system comprising an interface box comprising one or more electrical components for receiving electrical signals from EEG sensors, one or more electrical components for wirelessly transmitting electrical signals, and at least 12 input channels having at least 1 EEG channel connected to the one or more electrical components for receiving electrical signals, wherein the one or more electrical components for wirelessly transmitting electrical signals transmit at frequencies lower than 2.0 GHz. The system in this embodiment transmits data below these frequencies to avoid frequency bands that are highly congested, namely the 2.4 GHz band. Operation within these bands over 2.0 GHz may make interference problematic such as by limiting usable bandwidth. Additionally, if power is constant then operation at lower frequencies allows for greater operational range than at higher frequencies. Conversely, operation at lower frequencies consumes less power than higher frequencies over the same range.

In yet another embodiment the invention is a wireless EEG data acquisition system comprising an interface box comprising one or more electrical components for receiving electrical signals from EEG sensors, one or more electrical components for wirelessly transmitting electrical signals, at least 1 EEG channel connected to the one or more electrical components for receiving electrical signals, and one or more sensors for measuring and channels for airflow, tidal volume and ventilation rate; a processor. Preferably two pressure transducers, are used to measure oral and nasal airflow, tidal volume, ventilation rate and snore parameters. More preferably, these two pressure transducers are built into or attached to the interface box. That is snore can be derived without a microphone or other sensor. In addition this system allows for the use of only one sensor to measure airflow, tidal volume, ventilation rate, and snore parameters. Since one sensor, instead of the normal two or more, can obtain all the data needed for the above mentioned parameters system resources are freed up to allow for the addition of even more sensor inputs. Therefore the same information can be acquired with fewer sensors, thus reducing hardware costs and system resource requirements.

In still yet another embodiment the invention is a wireless EEG data acquisition system comprising an interface box comprising one or more electrical components for receiving electrical signals from EEG sensors, one or more electrical components for wirelessly transmitting electrical signals, and at least 1 EEG channel connected to the one or more electrical components for receiving electrical signals, wherein the system is capable of automatically conducting a RF sweep, to detect and display the occupied transmission frequency channels. This feature enables the user to see what frequencies are occupied to enable the user to efficiently choose a channel to use for data transmission.

In even still another embodiment the invention is a wireless EEG data acquisition system comprising an interface box comprising one or more electrical components for receiving electrical signals from EEG sensors, one or more electrical components for wirelessly transmitting electrical signals, and at least 12 input channels having at least 1 EEG channel connected to the one or more electrical components for receiving electrical signals, wherein the one or more electrical components for wirelessly transmitting electrical signals transmit at frequencies lower than 2.0 GHz and the system allows the user to manually select the transmission frequency within a band to avoid interference.

In even still another embodiment the invention is a wireless EEG data acquisition system comprising an interface box comprising one or more electrical components for receiving electrical signals from EEG sensors, one or more electrical components for wirelessly transmitting electrical signals, and at least 12 input channels having at least 1 EEG channel connected to the one or more electrical components for receiving electrical signals, wherein the one or more electrical components for wirelessly transmitting electrical signals transmit at frequencies lower than 2.0 GHz and the system is capable of automatically selecting a transmission frequency within a band to avoid interference. These features greatly improve the user's ability to avoid interference. While the system's automatic selection of transmission frequencies may be best suited for most users the manual capabilities allow users to pick frequencies they know to be less congested in their particular geographical location.

In even still another embodiment the invention is a wireless EEG data acquisition system comprising at least two interface boxes comprising one or more electrical components for receiving electrical signals from EEG sensors, one or more electrical components for wirelessly transmitting electrical signals, at least 1 EEG channel connected to the one or more electrical components for receiving electrical signals, and wherein each of the at least two interface boxes can be operated simultaneously without interfering with each other. Multiple systems, in a similar embodiment, are capable of operating simultaneously while using the same base station transceiver. These two capabilities allow for additional testing capability and capacity when multiple systems are used. Multiple systems can be used on multiple subjects in the same area without interference. Alternatively, multiple systems can be used on the same subject to collect a very large comprehensive amount of data on the physiological parameters of interest.

In even still another embodiment the invention is a wireless EEG data acquisition system comprising an interface box comprising one or more electrical components for receiving electrical signals from EEG sensors, one or more electrical components for wirelessly transmitting electrical signals, and at least 1 EEG channel connected to the one or more electrical components for receiving electrical signals and a receiver for accepting the wirelessly transmitted electrical signals from the interface box, wherein the receiver is powered through a USB port on a computer. Since the USB is the sole power source and data link for the base station and the receiver contained within it, simplifying setup so that no additional connections beside the USB are needed to setup the base station.

In even still another embodiment the invention is a wireless EEG data acquisition system comprising an interface box comprising one or more electrical components for receiving electrical signals from EEG sensors, one or more electrical components for wirelessly transmitting electrical signals, at least 1 EEG channel connected to the one or more electrical components for receiving electrical signals, and a removable memory for buffering or storage of data based at least in part on the electrical signals from the EEG sensors. This feature is most beneficial in that it allows for latter upgrades in buffering and storage capacity. Additionally it allows for the storage of data on multiple removable memory units for multiple test runs. Thus allowing the user to run multiple tests in one location, then transport the removable memory to another location for analysis while keeping the interface box at the first location to run further tests. Such a need may arise when emergency medical units need to test multiple subjects in the field, but have only a limited number of systems. Such a need may arise simply out of convenience for the user.

In even a further embodiment the invention is a wireless EEG data acquisition system comprising a) an interface box comprising one or more electrical components for receiving electrical signals from EEG sensors, one or more electrical components for wirelessly transmitting electrical signals, and at least 1 EEG channel connected to the one or more electrical components for receiving electrical signals b) a receiver for accepting the wirelessly transmitted electrical signals from the interface box and c) a video camera wherein the system is capable of transmission of video that can be time synchronized for display with physiological signals. This particular feature allows the user to see what the subject was doing during a certain physiological event or simply allow for more complete monitoring of the subject.

In even a further embodiment the invention is a wireless EEG data acquisition system comprising an interface box comprising one or more electrical components for receiving electrical signals from EEG sensors, one or more electrical components for wirelessly transmitting electrical signals, at least 1 EEG channel connected to the one or more electrical components for receiving electrical signals, and at least one sensor for outputting a signal related to a subject's motion, wherein the output signal related to the subject's motion can be used to eliminate artifacts in the signal from the sensors. Preferably the sensor that is outputting a signal related to the subject's motion is an accelerometer. Alternatively the sensor that is outputting a signal related to the subject's motion is a video camera. The presence of motion artifact can result in misdiagnosis, prolong procedure duration and can lead to delayed or inappropriate treatment decisions. Thus, it is imperative to remove motion artifacts from the biopotential signal to prevent these problems from occurring during treatment.

In even a further embodiment the present invention is a wireless EEG data acquisition system comprising an interface box comprising one or more electrical components for receiving electrical signals from EEG sensors, one or more electrical components for wirelessly transmitting electrical signals, at least 1 EEG channel connected to the one or more electrical components for receiving electrical signals, and at least one sensor for outputting a signal related to the subject's eye movement, wherein the output signal related to the subject's eye movement can be used to eliminate artifacts in the signal from the sensors. Preferably the sensor that is outputting a signal related to the subject's eye movement is an electrode or set of electrodes. The presence of ocular artifacts can result in misdiagnosis, prolong procedure duration and can lead to delayed or inappropriate treatment decisions. Thus, it is imperative to remove ocular artifacts from the biopotential signal to prevent these problems from occurring during treatment.

In even still a further embodiment the invention is a wireless EEG data acquisition system comprising a) an interface box comprising one or more electrical components for receiving electrical signals from EEG sensors, one or more electrical components for wirelessly transmitting electrical signals, and at least 1 EEG channel connected to the one or more electrical components for receiving electrical signals b) a receiver for accepting the wirelessly transmitted electrical signals from the interface box and c) a video camera having an output wherein the output from the video camera system can be used to eliminate artifacts in the signal from the EEG sensors. Most preferably at least one accelerometer and at least one video camera are sensors for monitoring the subject's motion that are used for eliminating motion artifacts. The presence of motion artifacts can result in misdiagnosis, prolong procedure duration and can lead to delayed or inappropriate treatment decisions. Thus, it is imperative to remove motion artifact from the biopotential signal to prevent these problems from occurring during treatment.

In even still a further embodiment the invention is a wireless sleep diagnosis device comprising electronic components for receiving signals from one or more sensors and wirelessly transmitting a signal based in part on the signal from the one or more sensors; and at least one airflow sensor for measuring a subject's nasal and/or oral breathing pattern.

In even still a further embodiment the invention is a wireless sleep diagnosis device comprising electronic components for receiving signals from one or more sensors including an EEG sensor and wirelessly transmitting a signal based in part on the signal from the one or more sensors; and at least one airflow sensor for measuring a subject's nasal and/or oral breathing pattern.

In even still a further embodiment the invention is a wireless sleep diagnosis device comprising electronic components for receiving signals from one or more sensors and wirelessly transmitting a signal based in part on the signal from the one or more sensors, at least one accelerometer and a case for holding and protecting the electronic components and the at least one accelerometer.

In even still a further embodiment the invention is a wireless sleep diagnosis device comprising electronic components for receiving signals from one or more sensors including an EEG sensor and wirelessly transmitting a signal based in part on the signal from the one or more sensors, at least one accelerometer and a case for holding and protecting the electronic components and the at least one accelerometer.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DESCRIPTION OF THE PREFERRED EMBODIMENTS

Figure 1:
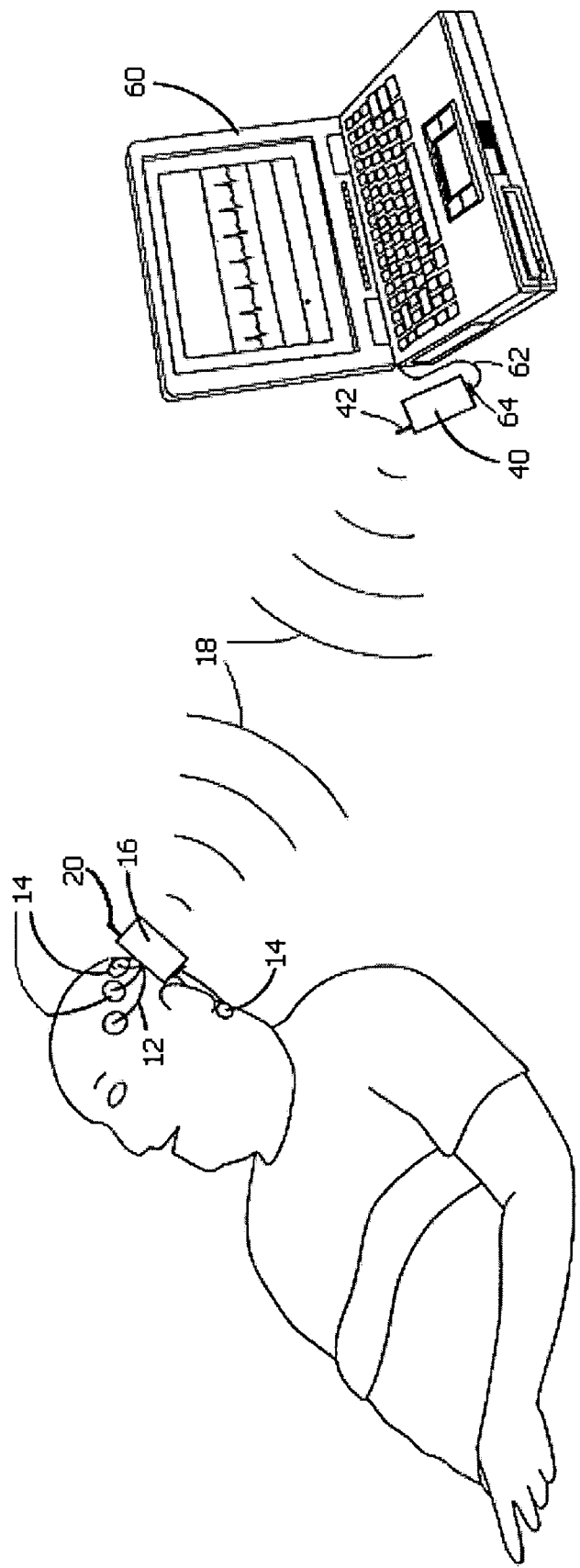
FIG. 1. Schematic representation of one embodiment of the EEG data acquisition system of the present invention in use with a subject to acquire EEG and/or other signals from the subject and then transmit them to the receiver and attached computer.

The present invention provides for a data acquisition system for EEG and other physiological conditions, preferably wireless, and method of using such system. The wireless EEG system can be used in a number of applications including both studies and clinical work. These include both clinical and research sleep studies, alertness studies, emergency brain monitoring, and any other tests or studies where a subject's or patient's EEG reading is required or helpful.

In various embodiments of the present invention include an interface box which is preferably used to protect one or more electrical components and allow for the connection of various sensors to the electrical components inside the interface box. The interface box is preferably intended to be secured to or held by the subject. The box will preferably have electrical connectors incorporated in to the structure of the interface box, so that various sensors can be connected to the box and through to the electrical components inside the interface box. Preferably the connectors incorporated into the interface box are no touch connectors which enable connections to commercially available electrodes and sensors. The interface box will also preferably have at least one air port connection to one or more internal sensors, such as one or more pressure transducers or other sensors. The interface box will also more preferably will have at least two air port connections to one or more internal sensors, such as one or more pressure transducers or other sensors. The interface box can be constructed from most any rigid material; including, but not limited to, various types of wood, various types of plastics, various types of polymers, various types of resin, various types of ceramics, various types of metals, and various types of composite materials. Preferably the box is constructed of an electrically insulative and light weight material such as a type of plastic, rigid polymer, fiberglass, carbon fiber composite, or other material with similar characteristics.

Sensors which are used with various embodiments of the present invention are described herein but can also be any of those known to those skilled in the art for the numerous applications of this device. These sensors include electrodes for measuring electro-physiological signals such as EEG, ECG, EMG, ENG, ERG, EOG and the like. These electro-physiological signals can be obtained by any method known in the art, or are envision to cover those sensors subsequently developed by those skilled in the art to detect these types of signals.

For example, the sensors can be magnetic sensors. Since electro-physiological signals are, in general, electrical currents which produce associated magnetic fields, the present invention further anticipates methods of sensing those magnetic fields to acquire brain wave signals similar to those which can be obtained through, for example, an electrode applied to the subject's scalp. The subject(s) referred to in the present invention can be any form of animal. Preferably the subject(s) are mammal, and most preferably human.

If electrodes are used to pick up the electro-physiological signals, these electrodes for example when measuring brain wave or EEG signals may be placed at one or several locations on the subject(s)' scalp or body. The electrode(s) can be placed at various locations on the subject(s) scalp in order to detect EEG or brain wave signals. Common locations for the electrodes include frontal (F), parietal (P), anterior (A), central (C) and occipital (O). Preferably for the present invention at least one electrode is placed in the occipital position. In order to obtain a good EEG or brain wave signal it is desirable to have low impedances for the electrodes. Typical EEG electrodes connections may have an impedance in the range of from 5 to 10 K ohms. It is in generally desirable to reduce such impedance levels to below 2 K ohms. Therefore a conductive paste or gel may be applied to the electrode to create a connection with an impedance below 2 K ohms. Alternatively or in conjunction with the conductive gel, the subject(s)' skin may be mechanically abraded, the electrode may be amplified or a dry electrode may be used. Dry physiological recording electrodes of the type described in U.S. Pat. No. 7,032,301 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired, the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

If electrodes are used to pick up the electro-physiological signals, these electrodes for example when measuring cardiac signals using an ECG, may be placed at specific points on the subject's body. The ECG is used to measure the rate and regularity of heartbeats as well as the size and position of the chambers, any damage to the heart and in diagnosing sleeping disorders. As the heart undergoes depolarization and repolarization, electrical currents spread throughout the body because the body acts as a volume conductor. The electrical currents generated by the heart are commonly measured by an array of preferably 12 electrodes, placed on the body surface. Although a full ECG test usually involves twelve electrodes, only two are required for many tests such as a sleep study. These are placed on the subject's left-hand ribcage, under the armpit and on the right-hand shoulder, near the clavicle bone. An ECG is important as a tool to detect the cardiac abnormalities that can be associated with respiratory-related disorders. Preferably electrodes are placed on each arm and leg, and six electrodes are placed at defined locations on the chest. The specific location of each electrode on a subject's body is well known to those skilled in the art and varies amongst individual and different types of subjects. These electrode leads are connected to a device contained in the signal processing module of the present invention that measures potential differences between selected electrodes to produce electrocardiographic tracings.

There are two basic types of ECG leads: bipolar and unipolar. Bipolar leads (standard limb leads) utilize a single positive and a single negative electrode between which electrical potentials are measured. Unipolar leads (augmented leads and chest leads) have a single positive recording electrode and utilize a combination of the other electrodes to serve as a composite negative electrode.

The subject's respirations can be measured by measurement of airflow, respiratory effort, oxygenation and ventilation, and the like. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound, snore sound, blood pressure and the like. Measurement of respiratory effort is preferably measured by esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer or other sensors, which can indirectly measure a subject's respirations and the variability of respirations by providing a signal which correlates to the thoracic/abdominal expansion/contractions of the subject's abdominal cavity. Respiration belts may be placed at one or several locations on the subject's torso or in any other manner known to those skilled in the art. Preferably, the respiration belts are positioned below the axilla and/or at the level of the umbilicus in order to measure rib cage and abdominal excursions. More preferably, if respiration belts are used then at least two belts are used one being positioned at the axilla and the other at the umbilicus.

Another example of such a sensor or method for measuring respirations either directly or indirectly is a nasal cannula or a facemask. The nasal cannula or facemask can be used to measure the subject's respiratory airflow. Nasal or oral airflow can be measured quantitatively and directly with a pneumotachograph consisting of a standard oxygen nasal cannula or facemask respectively connected to a pressure transducer and placed in the nose or over the subject's mouth and nose respectively. Airflow can be estimated by measuring nasal or oral airway pressure that decreases during inspiration and increases during expiration. Inspiration and expiration produce fluctuations on the pressure transducer's signal that is proportional to airflow. The oral and nasal components of these measurements can be acquired through the use of at least two pressure transducers, one transducer for each component. Preferably the two pressure transducers are internal to the interface box and have separate air ports for nasal and oral measurements. Through the use of software filtering, "snore signals" can also be obtained from a sole pressure transducer signal. The software filtering extracts the high frequency portion of the transducer signal to obtain the "snore signal." Thereby eliminating the need for a separate sensor, such as a microphone or another transducer, and also lessening the system resources needed to detect both snore and airflow. A modified nasal cannula or facemask may also be used which is connected to a carbon dioxide or oxygen sensor to measure respective concentrations of these gases. In addition a variety of other sensors can be connected with either a nasal cannula or facemask to either directly or indirectly measure a subject's respirations.

Still another example of such a sensor or method of either directly or indirectly measuring respirations of the subject is the use of a pulse oximeter. The pulse oximeter can measure the oxygenation of the subject's blood by producing a source of light originating from the oximeter at two wavelengths (650 nm and 805 nm). The light is partly absorbed by haemoglobin, by amounts which differ depending on whether it is saturated or desaturated with oxygen. By calculating the absorption at the two wavelengths the proportion of haemoglobin which is oxygenated can be estimated. Preferably, pulse oximeters are placed on a subject's earlobe or fingertip. More preferably, the pulse oximeter is placed on the subject's index finger. In one embodiment of the present invention a pulse oximeter is built in or hard wired to the interface box Other sensors can be used to measure various parameters of a subject's physiological condition. These other parameters are preferably measured using sensors or devices such as a photodetectors, accelerometers, pneumotachometers, strain gauges, thermal sensors, transducers, piezo sensors, magnetometers, pressure sensors, static charge-sensitive beds, audio monitors, video monitors and the like. Since the system is programmable potentially any transducer type sensor, that is any sensor that outputs an electrical signal, can be used with the system.

Preferably, the signals from one or more of the aforementioned sensors are fed into the connectors on the interface box. The interface box preferably comprises one or more electrical components which receive these signals, and then wirelessly transmit a signal based on these signals to another receiver. The interface box preferably comprises a processor or other receiver or device which ultimately receives these signals comprises a processor for analyzing the one or more signals from these sensors.

One preferable embodiment of this device is a programmable wireless data acquisition system. This programmable wireless data acquisition system is used to receive the signals from one of more sensors and work with an internal or external processor to analyze the signals. Physiological data is transmitted between the physiological sensors of types described above and the signal processing module using wireless technology. Preferably, the wireless technology is radio frequency based. Most preferably the wireless technology is digital radio frequency based. Preferably, the physiological data is processed to some extend directly in the interface box. More preferably, the physiological data is corrected for artifacts within the interface box. The physiological signals are transmitted wirelessly to a receiver which can be a base station, a transceiver hooked to a computer, a PDA, a cellular phone, a wireless network, or the like. Most preferably the physiological signals are transmitted wirelessly in digital format to a receiver which can be a base station, a transceiver hooked to a computer, a PDA, a cellular phone, a wireless network, or the like. Wireless signals are both received and transmitted via use of an antenna, preferably external. Frequencies used for transmission are preferably less than about 2.0 GHz. More preferably, frequencies used for transmission are primarily 902-928 MHz, but Wireless Medical Telemetry Bands (WMTS), 608-614 MHz, 1395-1400 MHZ, or 1429-1432 MHz can also be used. The present invention may also use other less preferable frequencies above 2.0 GHz for data transmission, including but not limited to such standards as Bluetooth, WiFi, IEEE 802.11, and the like. It is envisioned, but not as preferable that the communication between the interface box and base station or like device can also, or in addition to, be hardwired, instead of wireless. The physiological sensors are generally hard wired to the signal processing unit, but due to the ongoing evolution in wireless sensor technology, signals from physiological sensors will likely be transmitted wirelessly to the signal processing unit, or alternatively, directly to the base station having an integrated signal processing unit, and as such are considered to be part of the present invention. With the advances in MEMS sensor technology the sensors may have integrated analog amplification, integrated A/D converters, and integrated memory cells for calibration; allowing for some signal conditioning directly on the sensor before transmission.

The posture and movement of the subject can be a factor affecting the signal quality of the signals from the sensors. As such, various embodiments of the present invention include sensors, devices and methods of determining the posture and movement of the subject so this information can be used when analyzing the physiological signals. The posture and movement of the subject is preferably determined by signals received from an accelerometer or an array of two or more accelerometers. Accelerometers are known in the art and are suitable for use as a motion monitoring unit. Various other types of sensors besides accelerometers can be additionally or alternatively used in sensing the criteria (e.g., vibration, force, speed, and direction) used in determining motion. For particularly low power designs, the one or more sensors used can be largely mechanical.

Body movement of the subject will result in a high amplitude signal from the accelerometer. The microcontroller can also monitor the sensor signals for any indication that the subject has moved from a supine position to an upright position. For example, the integrated velocity signal computed from the vertical acceleration component of the sensor data can be used to determine that the subject has just stood up from a chair or sat up in bed. A sudden change in the vertical signal, particularly following a prolonged period with little activity while the subject is sleeping or resting, confirms that a posture-changing event occurred.

Errors in the form of noise can occur when biopotential data acquisition is performed on a subject. For example, a motion artifact is noise that is introduced to a biopotential signal that can result from motion of an electrode that is placed on the skin of a subject. A motion artifact can also be caused by bending of the electrical leads connected to an electrode or even some other sensors. The presence of motion artifacts can result in misdiagnosis, prolong procedure duration and can lead to delayed or inappropriate treatment decisions. Thus, it is imperative to remove motion artifact from the biopotential signal to prevent these problems from occurring during treatment.

For methods of the present invention it is important to reduce motion artifacts from the sensor placement. The most common methods for reducing the effects of motion artifacts in sensors such as electrodes have focused on skin deformation. These methods include removing the upper epidermal layer of the skin by abrasion, puncturing the skin in the vicinity of the electrode, and measuring skin stretch at the electrode site. The methods for skin abrasion ensure good electrical contact between the electrode and the subject's skin. In this method, an abrasive pad is mechanically rotated on the skin to abrade the skin surface before electrode placement. Moreover, medical electrodes have been used with an abrading member to prepare the skin after application of the electrode whereby an applicator gun rotates the abrading member. Methods of skin preparation that abrade the skin with a bundle of fibers have also been disclosed. The methods discussed above provide a light abrasion of the skin to reduce the electrical potential and minimize the impedance of the skin, thereby reducing motion artifacts. However, skin abrasion methods can cause unnecessary subject discomfort, prolong procedure preparation time and can vary based on operator experience. Furthermore, skin abrasions methods can lead to infection, and do not provide an effective solution to long term monitoring. Alternatively dry physiological recording electrodes could be used, instead of gel electrodes. Dry physiological recording electrodes of the type described in U.S. Pat. No. 7,032,301 are herein incorporated by reference. Dry physiological electrodes do not require any of the skin abrasion techniques mentioned above and are less likely to produce motion artifacts in general The above mentioned methods are indeed good practice to follow in the field as they reduce motion artifacts, but they do not completely eliminate motion artifacts. The invention possesses the ability to more completely remove motion and other artifacts by firmware and/or software correction that utilizes information collected preferably from a sensor or device to detect body motion, and more preferably from an accelerometer.

In certain embodiments of the present invention a 3-D accelerometer is directly connected to a microprocessing unit within the micromodule controller. The microprocessing unit receives signal inputs from the accelerometer and a set of EEG signals. The microprocessor applies particular tests and algorithmns comparing the two signal sets to correct any motion artifacts that have occurred. The processor in one embodiment applies a time synchronization test, which compares the EEG signal data to the accelerometer signal data synchronized in time to detect motion artifacts and then remove those artifacts. Alternatively the processor may apply a more complicated frequency analysis. Frequency analysis preferably in the form of wavelet analysis can be applied to the accelerometer and EEG signals to yield artifact detection. Yet another alternative is to create a neural net model to improve artifact detection and rejection. This allows for the system to be taught over time to detect and correct motion artifacts that typically occur during a test study. The above examples are only examples of possible embodiments of the present invention not limitations. The accelerometer data need not be analyzed before wireless transmission, it could be transmitted analyzed by a base station, computer or the like after transmission. As should be obvious to those skilled in the art that a 2-D accelerometer or an appropriate array of accelerometers could also be used. Gyroscopes could be used as well for these purposes.

In addition, a video camera can be used to detect subject movement and position, and the information then used to correct any artifacts that may have arisen from such movement. Preferably the camera is a digital camera. More preferably the camera is a wireless digital camera. Preferably, the video acquired from the camera is then processed so that the subject's movement and position are isolated from other information in the video. The movement and position data that are acquired from the video is then preferably analyzed by software algorithms. This analysis will yield the information needed to make artifact corrections of the physiological signals.

One specific embodiment of the present invention using video subject movement detection involves the use of specially marked electrodes. The electrodes can be any appropriate electrode known in the art. The only change to the electrode is that they preferably have predetermined high contrast marks on them to make them more visible to the video camera. These marking could be manufactured into the electrodes or simply be a sticker that is placed on the back of the electrodes. These markings will make it easier for the video system to distinguish the electrodes from the rest of the video image. Marking each visible electrode will allow for the calculation of the movement of each individual electrode; thus allowing for more accurate artifact correction.

Another specific embodiment of the invention does not require the use of markings on the electrodes, instead the system can detect subject movement from monitoring the actual movement of the subject's body. Software is applied to the video that isolates the position of the subject's body including limbs, then continues to monitor the motion of the subject.

There are numerous advantages to using video over other means of artifact detection and correction. Foremost, video allows for the calculation of movement artifacts from each individual electrode without the need for accelerometers. This makes the use of video very cost effective in relation to other available methods. The video also can be used in conjunction with the accelerometer data to correct for motion artifacts, thus increasing the precision and accuracy of the system's motion artifact correction capabilities.

Various embodiments of the present invention also allow for the flexible use of removable memory to either buffer signal data or store the data for later transmission. Preferably, nonvolatile removable memory can be used as a way to customize the system's buffering capacity and for complete storage of the data. The micro-module controller for the interface box can be programmed to send all signal data to the removable memory or the micro-module controller can be programmed to transmit all data to the base station. If the micro-module controller is programmed to transmit the signal data to the base station wirelessly the removable memory then acts as a buffer. If the interface box loses its wireless connection with the base station, remote communication station or the like, the interface box will temporarily store the data in the removable memory until the connection is restored and data transmission can resume. If however the micro-module controller is programmed to send all signal data to the removable memory for storage then the system does not transmit any information to the base station at that time. That data stored on the removable memory can be retrieved by either wireless transmission from the interface box to the base station or like, or by removing the memory and directly reading. The method of directly reading will depend on the format of the removable memory. Preferably the removable memory is easily removable, that can be removed instantly or almost instantly without tools. In the current embodiment the memory slot is located on the side of the interface box and protected by a plastic cover. The memory is preferably in the form of a card and most preferably in the form of a small easily removable card with an imprint (or upper or lower surface) area of less than about 2 sq. inches. If the removable memory is being used for data storage, preferably it should be of a type that can write data as fast as it is produced by the system, and to possess enough memory capacity for the duration of the test. These demands will obviously depend on the type of test being conducted, tests requiring more sensors, higher sampling rates and longer duration of testing will require faster write speeds and larger data capacity. The type of removable memory used can be almost any type that meets the needs of the test being applied. Some examples of the possible types of memory that could be used include but are not limited to Flash Memory such as CompactFlash, SmartMedia, Miniature Card, SD/MMC, Memory Stick or XD-Picture Card. Alternatively a portable hard drive, CD-RW burner, DVD-RW burner or other data storage peripheral could be used. Preferably, a SD/MMC-flash memory card is used due to its small size. A PCMCIA card is not preferable because of the size and weight.

Preferably, the invention is capable of conducting a RF sweep to detect an occupied frequency or possible interference. The system is capable of operating in two different modes "manual" or "automatic." In the manual mode the system conducts an RF sweep and displays the results of the scan on to the system monitor. The user of the system can then manually choose which frequency or channel to use for data transmission. In automatic mode the system conducts a RF sweep and automatically chooses which frequencies to utilize for data transmission. The system also employs a form of frequency hopping to avoid interference and improve security. The system scans the RF environment then picks a channel to transmit over based on the amount of interference occurring over the frequency range.

Multiple EEG data acquisition systems can be used or are capable of operating simultaneously in the same geographical area without causing interference between the operations of these systems. Preferably two or more subject's can be hooked up to the EEG data acquisition system of the present invention and operate simultaneously without interference and more preferably through one base station. More preferably at least four subject's can be hooked up to the EEG data acquisition system of the present invention and operate simultaneously without interference, even more preferably at least six subject's and most preferably at least eight subject's.

In various embodiments of the system of the present invention, the system also includes a base station, remote communication station or the like for receiving the transmitted signal from the EEG data acquisition device. Preferably the base station is powered by a Universal Serial Bus (USB) from a computer or similar device. The single USB connection provides the data connection to the computer and the power from the computer to the base station. This allows for quick and simple setup of the base station thereby improving the mobility of the system as a whole. The USB is also beneficial because an additional AC outlet is not needed for the base station. This makes the system when used with a portable laptop, properly equipped PDA or comparable device completely wireless. The USB specification provides a single 5 volt wire from which connected USB devices may power themselves. The bus is specified to deliver up to 500 mA. Because of these power limitation, the base station of the various embodiments of the present invention is unique. This is evidenced by the lack of wireless medical data acquisition systems that employ a base station that is powered solely by a USB connection with the exception of the current invention. It is also evidenced by the much higher power requirements of the other base stations employed by other wireless medical data acquisition systems.

Preferably, the RF link utilizes a two-way (bi-directional) data transmission. By using a two-way data transmission, data safety is significantly increased. By transmitting redundant information in the data emitted by the electrodes, the base station, remote communication station or the like is capable of recognizing errors and request a renewed transmission of the data. In the presence of excessive transmission problems such as, for example transmission over excessively great distances, or due to obstacles absorbing the signals, the base station, remote communication station or the like is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the base station, remote communication station or the like to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The base station, remote communication station or the like of various embodiments of the present invention can be any device known to receive RF transmissions used by those skilled in the art to receive transmissions of data. The base station, remote communication station or the like by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the base station, remote communication station or the like can further transmit data both to another device and/or back. Further optionally, two different remote communication stations can be used, one for receiving transmitted data and another for sending data. For example, with the EEG wireless data acquisition system of the present invention, the base station, remote communication system or the like can be a wireless router, which establishes a broadband Internet connection and transmits the physiological signal to a remote Internet site for analysis, preferably by the subject's physician. Another example is where the base station, remote communication system or the like is a PDA, computer or cell phone, which receives the physiological data transmission, optionally re-processes the information, and re-transmits the information via cell towers, land phone lines or cable to a remote site for analysis. Another example is where the base station, remote communication system or the like is a computer or processor, which receives the data transmission and displays the data or records it on some recording medium, which can be displayed or transferred for analysis at a later time.

The digitized kinetic or physiological signal is then transmitted wirelessly to a base station, remote communication station or the like. This base station, remote communication station or the like allows the subject wide movement. Preferably, the base station, remote communication station or the like can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The base station, remote communication station or the like can be used to re-transmit the signal based in part from the physiological signal from the base station, remote communication station or the like wirelessly or via the Internet to another monitor, computer or processor system. This allows the physician or monitoring service to review the subjects physiological signals and if necessary to make a determination, which could include modifying the patients treatment protocols.

Wireless data acquisition systems are known in the art and perform similarly to the type described in U.S. Pat. No. 6,167,258 and is herein incorporated by reference. The one or more electronic components which are used in the EEG data acquisition system of the various embodiments of the present invention are outlined below. In FIG. 1, there is shown a block diagram outlining the one or more electronic components in more detail. In FIG. 1, a signal processing module 16 receives input 12 from an external sensor 14. This sensor 14 can be an EEG electrode or any of the other sensors described herein or known in the art. Although, one sensor 14 and one external input 12 are shown, the signal processing module 16 is capable of accepting multiple external inputs 12 from multiple sensors 14. In a very simple embodiment of the present invention, the signal processing module 16 generates a signal 18 encoded with data corresponding to the external input 12. The signal processing module 16 transmits the signal 18 by wireless means to base station 40. In FIG. 1, the wireless means is shown as radio frequency (RF). In this case, the signal processing module generates a radio frequency signal 18 by frequency modulating a frequency carrier and transmits the radio frequency signal through module antenna 20. The base station 40 receives the radio frequency signal 18 through base antenna 42, demodulates the radio frequency signal 18, and decodes the data. It is understood that other wireless means can be utilized with the present invention, such as infrared and optical, for example. However, RF wireless transmission is preferred. Although one module antenna 20 and one base antenna 42 is shown in this embodiment, it is understood that two or more diversity antennas can be used and are included in the present invention. An external programming means 60, shown in FIG. 1 as a personal computer, contains software which is used to program the signal processing module 16 and the base station 40 through data interface cable 62. The data interface cable 62 is connected to the base station 40 by connector 64. The signal processing module 16 and the base station 40 can be programmed by radio frequency (or other type) of signals transmitted between a base station 40 to the signal processing module 16 or to another base station 40. RF signals, therefore, can be both transmitted and received by both signal processing module 16 and base station 40. In this event the signal processing module 16 also includes a module receiver 29 while the base station 40 also includes a base transmitter 84, in effect making both the signal processing module 16 and the base station 40 into transceivers. In addition, the data interface cable 62 also can be used to convey data from the base station 40 to the external programming means 60. If a personal computer is the external programming means 60, it can monitor, analyze and display the data in addition to its programming functions. The base receiver 80 and module receiver 29 can be any appropriate receivers, such as direct or single conversion types. The base receiver 80 preferably is a double conversion superheterodyne receiver while the module receiver 29 preferably is a single conversion receiver. Advantageously, the receiver employed will have automatic frequency control to facilitate accurate and consistent tuning of the radio frequency signal 18 received thereby.

Figure 2:
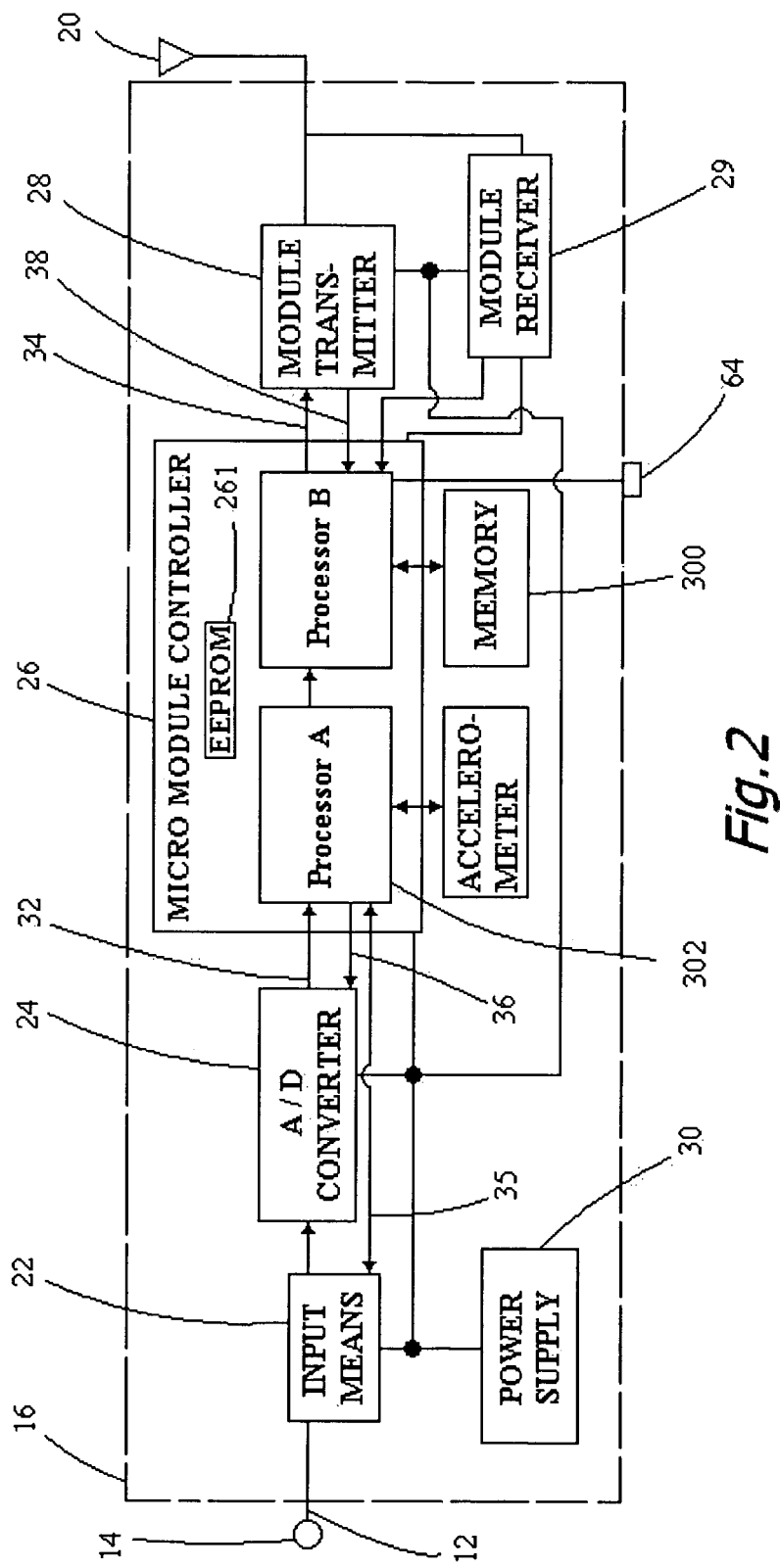
FIG. 2 Block diagram of one embodiment of the signal processing module of the present invention.

Referring now to FIG. 2, there is shown a block diagram of the signal processing module 16 with the sensor 14 and the module antenna 20. The signal processing module 16 comprises input means 22, analog-to-digital (A/D) means 24, a module microcontroller 26 with a nonvolatile memory, advantageously, an EEPROM 261, a module transmitter 28, a connection to removable memory 300, a module receiver 29 and a module power supply 30. Although the module antenna 20 is shown externally located from the signal processing module 16, it can also be incorporated therein. The module antenna 20 may be a printed spiral antenna printed on a circuit board or on the case of the signal processing module 16 or other type of antenna. A module power supply 30 provides electrical power to the signal processing module 16 which includes the input means 22, A/D means 24, module microcontroller 26, module transmitter 28 and module receiver 29. Additionally the signal processing module will preferably contain an accelerometer connected to a microprocessor 302 for position detection, motion detection, and motion artifact correction.

The input means 22 is adjustable either under control of the module microcontroller 26 or by means of individually populatable components based upon the specific external input 12 characteristics and range enabling the input means 22 to accept that specific external input 12. For example, if the input is a 4-20 mA analog signal, the input means 22 is programmed by the module microcontroller 26 and/or populated with the components needed to accept that range and characteristic of signals. If the input characteristics change the programming and/or components change accordingly but the same platform circuit board design is utilized. In other words, the same platform design is utilized notwithstanding the character, range, or quantity (number of external inputs 12) [up to a predetermined limit] of the input. For example, bioelectric signals such as EEG, EMG, EKG, EOG or the like have typical amplitudes of a few microvolts up to a few tens of millivolts. For a given application, a specific frequency band of interest might be from 0.1 Hz to 100 Hz, whereas another application may require measurement of signals from 20 Hz to 10 KHz. Alternatively, measurement of vital signs such as body temperature and respiration rate may deal with signals in a range of +5 volts, with a frequency content from DC (0 Hz) to 20 Hz. For other medical applications, the information of interest may be contained in the signal as a current, current loop sensor, or it may take the form of resistance, impedance, capacitance, inductance, conductivity, or some other parameter. The present invention provides a single device for measuring such widely disparate signal types and presents distinct economic advantages, especially to small enterprises such as a medical clinic located in a rural area, which would be empowered by this invention to conduct tests which would otherwise have required patient travel to a large medical center, with all the attendant cost thereof.

These capabilities are possible due to the selectively adaptable input means 22 and A/D means 24, the frequency agile module transmitter 28 and base transmitter 84, and the programmability of the module microcontroller 26 and EEPROM 261. One universal platform design then can be utilized for all applications. In addition, the signal processing module can comprise multiple copies of the input means 22 and the A/D means 24. Cost savings can be achieved by multiplexing at several different points in the input means 22 and the A/D means 24 allowing hardware to be shared among external inputs 12.

After receipt by the input means 22, the external input 12 is inputted to the A/D means 24. The A/D means 24 converts the input to a digital signal 32 and conditions it. The A/D means 24 utilizes at least one programmable A/D converter. This programmable A/D converter may be an AD7714 as manufactured by Analog Devices or similar. Depending upon the application, the input means 22 may also include at least one low noise differential preamp. This preamp may be an INA126 as manufactured by Burr-Brown or similar. The module microcontroller 26 can be programmed to control the input means 22 and the A/D means 24 to provide specific number of external inputs 12, sampling rate, filtering and gain. These parameters are initially configured by programming the module microcontroller 26 to control the input means 22 and the A/D means 24 via input communications line 35 and A/D communications line 36 based upon the input characteristics and the particular application. If the application changes, the A/D converter is reconfigured by reprogramming the module microcontroller 26. In this manner, the input means 22 and the A/D means 24 can be configured to accept analog inputs of 4-20 mA, +/-5 volts, +/-15 volts or a range from +/-microvolts to millivolts. They also can be configured to accept digital inputs for digital applications such as detection of contact closure for example.

The module microcontroller 26 controls the operation of the signal processing module 16. In the present invention, the module microcontroller 26 includes a serial EEPROM 261 but any nonvolatile memory (or volatile memory if the signal processing module remains powered) can be used. The EEPROM 261 can also be a separate component external to the module microcontroller 26. Advantageously, the module microcontroller 26 may be PIC16C74A PIC16C74B or a PIC16C77 both manufactured by Micro-Chip, or an Amtel AT90S8515 or similar. The module microcontroller may advantageously contain two microprocessors in series as shown in FIG. 2. The module microcontroller 26 is programmed by the external programming means 60 through the connector 64 or through radio frequency signal from the base station 40. The same module microcontroller 26, therefore, can be utilized for all applications and inputs by programming it for those applications and inputs. If the application or inputs change, the module microcontroller 26 is modified by merely reprogramming. The digital signal 32 is inputted to the module microcontroller 26. The module microcontroller 26 formats the digital signal 32 into a digital data stream 34 encoded with the data from the digital signal 32. The digital data stream 34 is composed of data bytes corresponding to the encoded data and additional data bytes to provide error correction and housekeeping functions. Advantageously, the digital data stream 34 is organized in data packets with the appropriate error correction data bytes coordinated on a per data packet basis. These packets can incorporate data from a single input channel or from several input channels in a single packet, or for some applications may advantageously include several temporally differing measurements of one or a plurality of input channels in a single packet. The digital data stream 34 is used to modulate the carrier frequency generated by the transmitter 28.

The module transmitter 28 is under module microcontroller 26 control. The module transmitter 28 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 34 is used to frequency modulate the carrier frequency resulting in the radio frequency signal 18 which is then transmitted through the module antenna 20. The generation of the carrier frequency is controlled by the module microcontroller 26 through programming in the EEPROM 261, making the module transmitter 28 frequency agile over a broad frequency spectrum. In the United States and Canada a preferred operating band for the carrier frequency is 902 to 928 MHz. The EEPROM 261 can be programmed such that the module microcontroller 26 can instruct the module transmitter 28 to generate a carrier frequency in increments between 902 to 928 MHz. as small as about 5 to 10 KHz. In the US and other countries of the world, the carrier frequency may be in the 902-928 MHZ, Wireless Medical Telemetry Bands (WMTS), 608-614 MHz, 1395-1400 MHZ, or 1429-1432 MHz or other authorized band. This allows the system to be usable in non-North American applications and provides additional flexibility.

The voltage controlled crystal oscillator (not shown) in the module transmitter 28, not only provides the reference frequency for the module transmitter 28 but, advantageously also, provides the clock function 38 for the module microcontroller 26 and the A/D means 24 assuring that all components of the signal processing module 16 are synchronized. An alternate design can use a plurality of reference frequency sources where this arrangement can provide certain advantages such as size or power consumption in the implementation.

The module receiver 29 in the signal processing module 16 receives RF signals from the base station 40. The signals from the base station 40 can be used to operate and control the signal processing module 16 by programming and reprogramming the module microprocessor 26 and EEPROM 261 therein.

Figure 3:
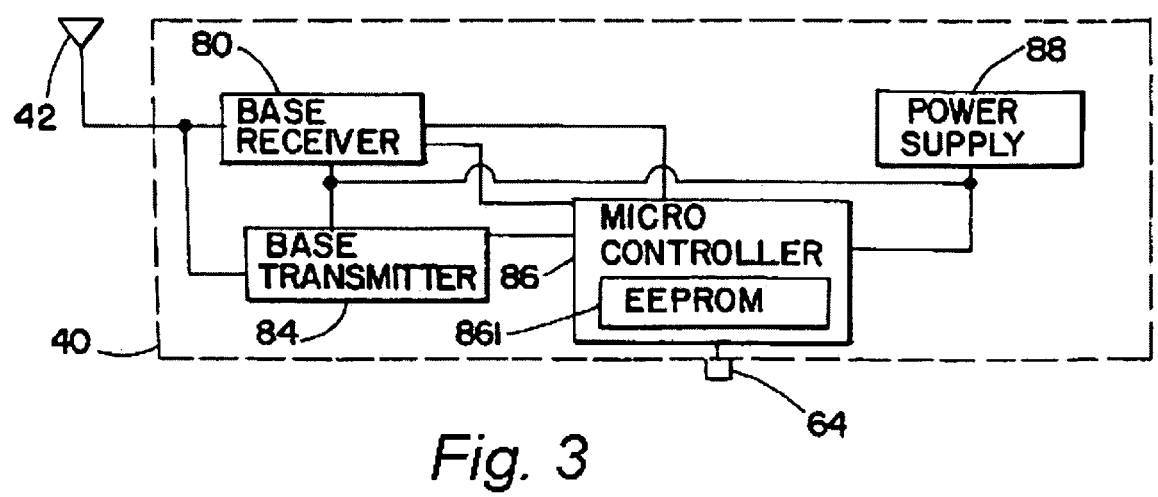
FIG. 3 Block diagram of one embodiment of the base station of the present invention.

Referring now to FIG. 3, the base station 40 has a base antenna 42 through which RF signals 18 are received. Base microcontroller 86 controls the operation of the base station 40 including base receiver 80, base transmitter 84, and base power supply 88. Base receiver 80 receives the RF signal 18 from base antenna 42. The base receiver 80 demodulates the RF signal 18 and the base microcontroller 86 removes any error correction and performs other housekeeping tasks. The data is then downloaded through connector 64 to the external programming means 60 or other personal computer (PC) or data storage/viewing device for viewing in real time, storage, or analysis, or is downloaded to removable memory of some form.

Figure 4:
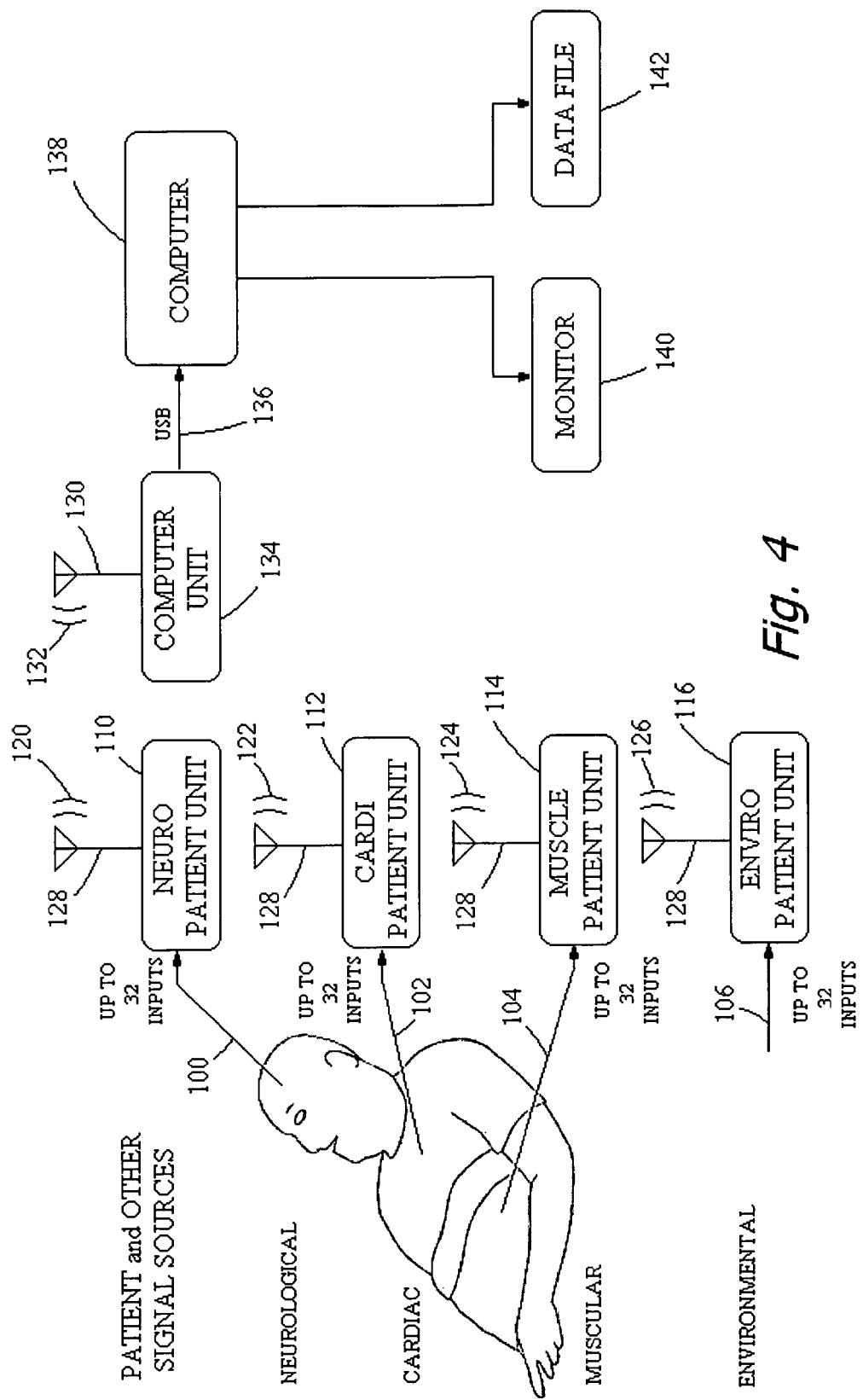
FIG. 4. Schematic representation of one embodiment of the present invention showing multiple interface boxes being used on a single subject, wherein the interface boxes are transmitting to a single receiver.

FIG. 4 is a schematic diagram of a multi-task monitoring system. In FIG. 4, a patient or subject is shown having their neurological 100, cardiac 102, muscular 104 and other environmental conditions 106 measured by sensors (not shown) and input into four separate data acquisition units 110, 112, 114, and 116. Each unit 110, 112, 114, and 116 can accept up to 32 inputs per unit. The units transmit signals 120, 122, 124, and 126 at different wireless radio frequencies from their respective antennas 128. The signals 120, 122, 124 and 126 do not interfere with each other because they have been manually or automatically selected to reduce interference as described earlier in the application. The signals can be received 132 simultaneously or in some order fashion by the antenna 130 on the receiving unit 134. The receiving unit 134 is both data and electrically connected via a USB connection 136 to a main processor or computer 138. The physiological signals are then processed or further processed, depending on whether processing took place in the data acquisition units 110, 112, 114, and 116, by the computer 138 and that information or data can be output to a monitor 140 or into a data file 142.

Figure 5:
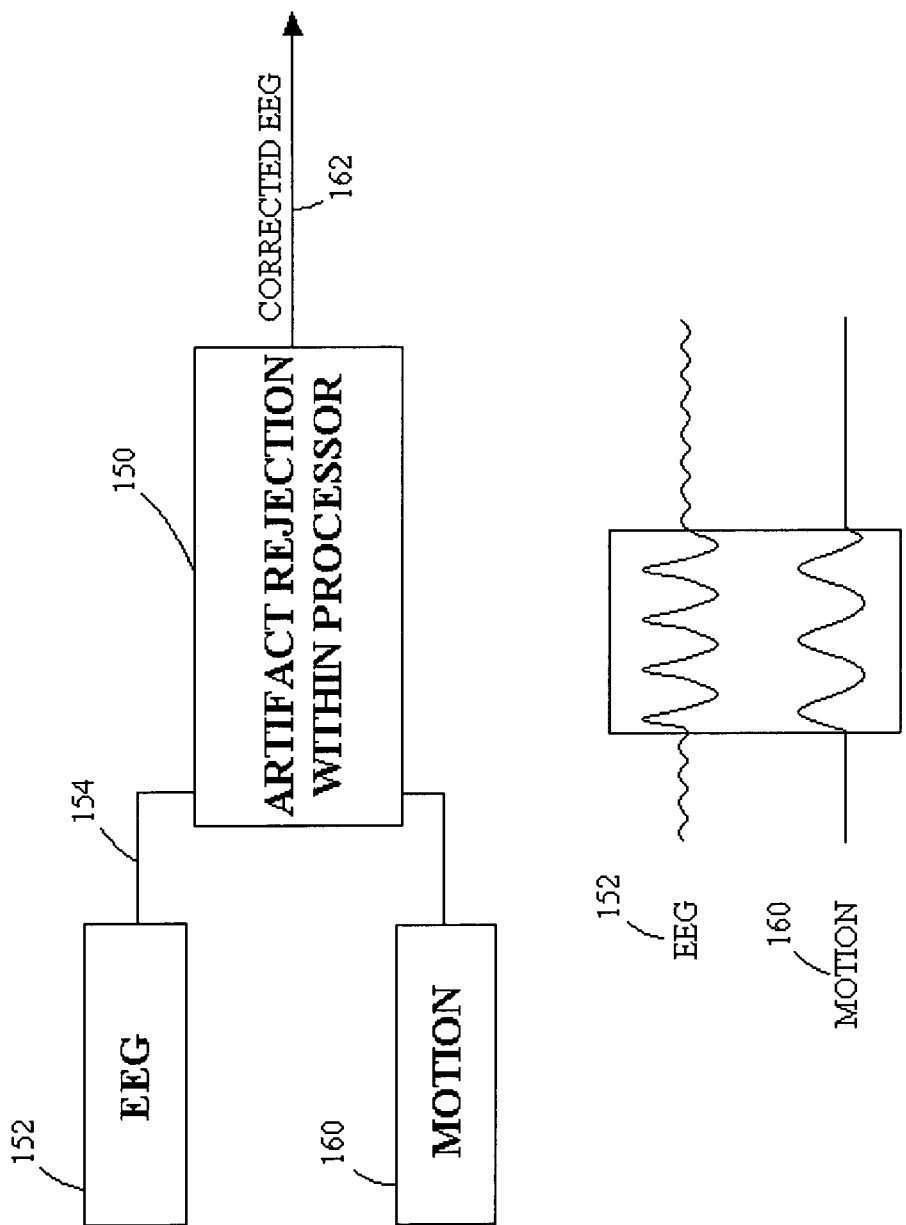
FIG. 5. Block diagram of one embodiment of the present invention showing the motion artifact rejection process.

FIG. 5 is a diagram of an artifact rejection module 150 that can be used in either the data acquisition system (not shown) or a computer or processor (not shown) linked to the data acquisition unit of the present invention. In FIG. 5, a subject's EEG signal 152 is preferably continuously fed 154 into artifact rejection algorithms within the data acquisition unit processor. Simultaneously sensor signals 160 from the subject's movement or motion are also fed into the artifact rejection processor so the EEG signal can be corrected 162 for effects of abnormal or prejudicial motion by the subject. The sensors for determining the subject's motion are described above, but the most preferred is an accelerometer which is incorporated into the EEG data acquisition unit itself.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A sleep diagnostic data acquisition system comprising:
    a. a first software stored on a non-transitory computer readable medium and executable by a first processor, the software configured to be loaded on a cell phone or a first computer comprising a first wireless transceiver and the first processor;
    b. a portable, wearable interface box adapted to be secured to a test subject at a first location and providing a single device for measuring and then wirelessly transferring sleep data from at least four sensors used for diagnosing sleep disorders,
        the portable, wearable interface box comprising
            i) an enclosure of a rigid material;
            ii) a battery;
            iii) one or more electrical components within the interface box for receiving electrical signals from the at least four sensors each having a signal, the one or more electrical components including a signal processing unit for receiving the electrical signals from the at least four sensors, the sensors which are attached to the subject or within the interface box that is secured to the subject, the sensors further which are hardwired to connect through at least one connector of the portable, wearable interface box and/or are built within the interface box, the signal processing unit including one or more input channels and further adapted for receiving and processing the sleep data from the one or more input channels;
            iv) one of the at least four sensors for measuring and/or deriving airflow and/or snore;
            v) a nonvolatile memory for storage of the sleep data from the one or more input channels; and
            vi) a second wireless transceiver adapted for operating at frequencies above 2 GHz using a Bluetooth protocol and transmitting the sleep data collected with the portable, wearable interface box wirelessly to the first wireless transceiver of the cell phone or the first computer with the first software loaded;
    c. the at least four sensors are selected from a group consisting of: accelerometer(s), pulse oximeter(s) including fingertip pulse oximeter(s) and those built into the portable, wearable interface box, rip belt(s), respiratory effort belt(s), pressure sensor(s), microphone(s), strain gauge(s), pressure transducer(s), and transducer(s), the at least four sensors adapted
        1) To be applied to the subject, a first and second of the at least four sensors adapted to be applied to a finger, arm and/or torso of the subject;

2) To measure or derive airflow or snore, respiratory effort, blood oxygenation and body position of the subject during testing; and 3) To be electrically hardwired and/or releasably connected to the portable, wearable interface box adapted to be worn by the subject;

d. an at least second software stored on a non-transitory computer readable medium and executable by a second computer, a second processor, and/or a monitor at one or more sites remote to the first location;

e. the first software, when executed by the first processor of the cell phone or the first computer, configured to wirelessly receive and re-transmit the sleep data, or optionally send the sleep data further processed with the first processor of the cell phone or the first computer, with the at least one first wireless transceiver over cell towers to the second computer or the second processor for analysis;

f. the second software when executed by the second computer or the second processor configured to analyze the sleep data at the one or more sites remote from the first location where the sleep data was collected; and g. the at least second software, when executed by the monitor or the second computer, configured to display both, in part, the sleep data and analyzed sleep data to allow for diagnosis of a sleep disorder and, if necessary, modify a sleep treatment of the subject.

2. The sleep diagnostic data acquisition system of claim 1, wherein a third of the at least four sensors measures airflow and comprises a nasal cannula or a facemask, a first pressure sensor or pressure transducer internal to the portable, wearable interface box, and a first air port adapted for connecting the nasal cannula or facemask to the first pressure sensor or pressure transducer.

3. The sleep diagnostic data acquisition system of claim 2, wherein the second sensor measures respiratory effort and comprises a respiratory effort belt, a second pressure sensor or pressure transducer internal to the portable, wearable patient interface box, and a second air port adapted for connecting the respiratory effort belt to the second pressure sensor or pressure transducer.

4. The sleep data acquisition system in claim 1, wherein the interface box further includes an A/D converter that is multiplexed for the signals from the one or more input channels.

5. The sleep data acquisition system in claim 2, wherein the interface box further includes an A/D converter that is multiplexed for the signals from the one or more input channels.

6. The sleep data acquisition system in claim 3, wherein the interface box further includes an A/D converter that is multiplexed for the signals from the one or more input channels.

7. The sleep data acquisition system in claim 2, wherein one of the at least four sensors is a pressure sensor or a pressure transducer, and further comprising a software filter configured to extract a high frequency portion of the signal of the first pressure sensor or pressure transducer to obtain a snore signal.

8. The sleep data acquisition system in claim 3, wherein one of the at least four sensors is a pressure sensor or a pressure transducer, and further comprising a software filter configured to extract a high frequency portion of the signal of the first pressure sensor or pressure transducer to obtain a snore signal.

9. The sleep data acquisition system in claim 7, wherein the software filter is adapted to determine airflow, tidal volume, ventilation rate and snore detection from the first pressure sensor or pressure transducer.

10. The sleep data acquisition system in claim 8, wherein the software filter is adapted to determine airflow, tidal volume, ventilation rate and snore detection from the first pressure sensor or pressure transducer.

* * * * *